United States Patent [19]

Ambrus et al.

[11] 4,363,910

[45] Dec. 14, 1982

[54] 2,2-DIMETHYL-1,2-DIHYDROQUINOLINE DERIVATIVES USEFUL AS ANTIOXIDANTS

[75] Inventors: Dezsö Ambrus; Tamas Szabolcsi; Istvan Hutas, all of Budapest, Hungary

[73] Assignee: Chinoin Gyogyszer es Vegyeszeti Termekek Gyara R.T., Budapest, Hungary

[21] Appl. No.: 121,810

[22] Filed: Feb. 15, 1980

[30] Foreign Application Priority Data

Feb. 21, 1979 [HU] Hungary .............................. CI 1916

[51] Int. Cl.$^3$ .......................................... C07D 215/36
[52] U.S. Cl. .................................... 546/172; 426/545
[58] Field of Search ................... 426/545, 447, 2, 74; 546/172; 252/405, 406

[56] References Cited

U.S. PATENT DOCUMENTS

| 2,562,970 | 8/1951 | Thompson | 426/545 |
| 3,325,288 | 6/1967 | Tung | 426/545 |
| 3,347,677 | 10/1967 | Jaworski | 426/545 |

OTHER PUBLICATIONS

J. Chem. Soc. 1933, p. 1327–Cliffe.

*Primary Examiner*—Hiram Bernstein
*Attorney, Agent, or Firm*—Karl F. Ross

[57] ABSTRACT

(2,2-Dimethyl-1,2-dihydroquinoline-4-yl)-methylsulfonic acid and the ammonium, alkali metal, alkali earth metal and zinc salts thereof are disclosed. The new compound and its salts are superior antioxidants useful to stabilize animal feedstuffs containing biologically active substances which are sensitive to oxidation.

3 Claims, No Drawings

2,2-DIMETHYL-1,2-DIHYDROQUINOLINE DERIVATIVES USEFUL AS ANTIOXIDANTS

This invention relates to new 2,2-dimethyl-1,2-dihydroquinoline derivatives, to a process for the preparation thereof and to compositions containing them. More particularly, this invention relates to the new (2,2-dimethyl-1,2-dihydroquinoline-4-yl)-methylsulfonic acid and the salts thereof as well as to a process for the preparation of these compounds. (2,2-Dimethyl-1,2-dihydroquinoline-4-yl)-methylsulfonic acid and the salts thereof have valuable antioxidizing properties and accordingly, can be used as antioxidants in various mixtures. These mixtures and the use of the new 2,2-dimethyl-1,2-dihydroquinoline derivatives as antioxidants are also within the scope of the invention.

The feedstuffs used in huge quantities in the animal husbandry always contain biologically active substances which are sensitive to oxidation. These substances are generally stabilized by antiodixants, which should be devoid of any injurious effect to the living organism in the effective concentration and should be discharged rapidly, without leaving behind any residue.

It is well known that certain 1,2-dihydroquinoline derivatives have valuable antioxidizing properties. The preferred representatives of these compounds are for example disclosed in the Hungarian Pat. Nos. 149,469; 157,370; 161,563 and 162,358; in the South-African Pat. No. 712,702 and in the Japanese Pat. Nos. 70,48-11,103.

The commercially available 1,2-dihydroquinoline antioxidants are dark colored, not uniform, viscous or amorphous substances. Due to their good solubility in lipoids and poor water-solubility these compounds can be accumulated in the fatty tissues of the animal organism and may cause the discoloration thereof.

The present invention provides a well-defined, uniform, water-soluble antioxidant which has a wide-ranging applicability.

(2,2-Dimethyl-1,2-dihydroquinoline-4-yl)-methylsulfonic acid—described below as simply the "sulfonic acid"—and the salts thereof can be prepared by sulfonating 2,2,4-trimethyl-1,2-dihydroquinoline under mild conditions in an appropriately chosen reaction medium and if desired, converting the product obtained into a salt thereof.

The sulfonation reaction proceeds according to the following reaction scheme:

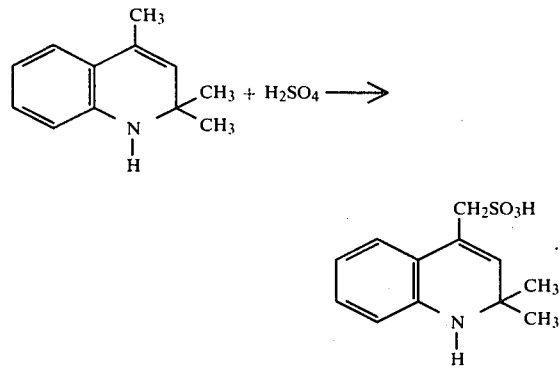

The term "mild conditions" is used herein to define reaction conditions which ensure that undesired side reactions are avoided. When strong sulfonating agents, for instance oleum are used, the dihydroquinoline molecule is sulfonated in the 7-position [W. H. Cliffe, J. Chem. Soc. 1933, p. 1327]. Sulfonation is carried out in the temperature range of 20° to 80° C., preferably between 35° and 45° C. Preferred sulfonating agents are sulfuric acid, chlorosulfonic acid and/or sulfuric trioxide.

The term "appropriately chosen reaction medium" as used herein refers to organic solvents which do not react with the sulfonating agents used. Preferably chlorinated hydrocarbons such as methylene chloride, carbontetrachloride; saturated hydrocarbons such as gasoline; and saturated heterocyclic compounds such as dioxane are used as a reaction medium.

The sulfonic acid obtained is preferably directly converted into a corresponding salt by using known basic reactants, preferably hydroxides, carbonates or acetates of monovalent and two-valent cations, such as ammonium, alkaline metal and alkali earth metal cations, e.g. sodium, potassium, magnesium and calcium ions or other metal ions, for example iron and zinc ions.

The salts are preferably isolated from the reaction mixture by pouring the mixture onto ice, followed by extraction with acetone and a subsequent evaporation. The salts can be further purified by recrystallization. The products obtained can contain water of crystallization, which can be eliminated by heating or for example by boiling with toluene. The free sulfonic acid can be recovered from a salt thereof preferably by using a cation exchange resin.

2,2,4-Trimethyl-1,2-dihydroquinoline used as a starting material in the process according to the invention is for example disclosed in the Hungarian Pat. No. 149,469. According to this patent said compound is prepared by reacting 1 mole of aniline with 2 moles of acetone in the presence of a suitable catalyst.

The valuable antioxidative properties of the sulfonic acid according to the invention are illustrated by the data listed in Table 1. The data set forth in Table 1 are the average results of numerous comparative tests. As a test material sunflower oil was used, which had previously been released from natural oxidants. The samples were kept in an uncovered round bottomed flask at 28° C. The peroxide number was determined by WEHLER's method, at intervals indicated in the table. From the results obtained it can be concluded that the antioxidizing activity of the compounds according to the invention is superior to that of the compounds used for comparision.

In another test—carried out in numerous repetitions—the carotene-preserving activity of the compounds according to the invention was tested on lucerne meal in comparision with samples devoid of any antioxidizing agent and with a commercially used antioxidant "BHD".

The change in the carotene content of lucerne meal was examined under natural conditions, at 26° C., under a relative humidity of 70%, in scattered light. The results obtained are summerized in Table 2. The results clearly show that the new compounds according to the invention have a significant and excellent carotene-preserving activity.

The compounds according to the invention due to their low toxicity, excellent antioxidizing and favorable physical properties, e.g. microcrystalline structure, powdery state, good water-solubility, white colour, can advantageously be used in the pharmaceutical, cosmetic and food industry, in the production of synthetic materials and rubber, which are the typical fields of application of antioxidants. It is especially preferred to use them in fodder mixtures, nutriments and premixes.

The antioxidants are preferably introduced into the fodder mixtures by means of additives and/or premixes. In this way the oxidizable substances which are absolutely necessary for keeping the biological equilibrium of fodders ($\beta$-carotene, A-, E-, D-vitamins etc.) are stabilized already in the initial phase of application. The stabilization is of primary importance when the premixes contain also microelements catalyzing the oxidation.

According to an aspect of the invention there are provided mixtures containing oxidation-sensitive substances, in which a compound according to the invention is present in an amount of 0.001 to 10% by weight. The use of these mixtures is also within the scope of the invention.

The compounds according to the invention are advantageously used in premixes, fodder additives, fodder mixtures and nutriments and ensure that these mixtures can be stored for a long time without any change in the easily oxidizable, biologically active substances contained therein.

The premixes and fodder additives contain the antioxidants according to the invention in the range of 100 to 100 000, depending on the field of application. It is preferred to form a homogenous mixture from the antioxidant and the oxidation-sensitive substance, which is then supplemented with the further components of the premix or fodder additive. The premixes contain for example dry seeds of fodder or various products of mill industry as a carrier. The premixes are then admixed with other fodder components and converted into fodders ready for consumption.

Some typical fodder ingredients are cob meal, bran, soya meal, fish meal, beet sugar, wheat meal, lucerne meal, sunflower extract. As a fodder supplement dicalcium phosphate, fodder lime, fodder salt, fodder briquette can be used. Additionally, various diluents, solvents, lubricants, carriers and other formulating agents can also be used in the fodder additives. By using the above listed ingredients the fodder additives can be formulated as powders, granules, powder mixtures, solutions, emulsions etc.

The nutriments and fodder mixtures contain 0.001 to 1% by weight of the antioxidants according to the invention.

The sulfonic acid salts according to the invention can be introduced into the nutriments or fodder mixtures not only in admixture with the premixes containing oxidation-sensitive substances, but also as so called "antioxidant premixes" or "antioxidant lipoid mixtures". In this case the antioxidants are admixed with indifferent materials and lipoids, respectively and the formed antiodixant premixes or antioxidant lipoid mixtures are added into the nutriments or fodder mixtures. The antioxidant lipoid mixtures if desired, can contain also emulsifying agents.

An important advantage of the sulfonic acid and the salts thereof according to the invention over the known antioxidants consists in the fact that in a concentration of 0.001 to 1% by weight they show no toxicity. They are well-defined, microcrystalline, white, powdery substances, with a good water-solubility, and can be incorporated into premixes, fodder additives, nutriments and fodder mixtures by conventional techniques.

The antioxidants according to the invention do not accumulate in the animal organism and are rapidly discharged. For example in poultry fed with nutriments which had been stabilized with the aforementioned sulfonic acid no harmful residue could be detected. Due to their fodder stabilizing activity, the instant antioxidants promote the weight gain of the animals.

The antioxidants according to the invention can advantageously be combined with known, lipophilic antioxidants, especially when the substance liable to oxidation is also strongly lipophilic. A preferred combination is a 2:1 mixture of the sodium salt of the sulfonic acid according to the invention and the known Etoxiquine (see Table 1).

In four-times its usual concentration (about 1000 ppm) the sodium salt of the sulfonic acid according to the invention has a strong activity in protecting sunflower oil from growing rancid (see Table 1). This fact is of particular interest first of all when longer storage is unavoidable. It is to be noted that the known antioxidants provide no protection when used in concentrations exceeding the usual level.

Further details of the invention are to be found in the following examples which are for illustration only.

EXAMPLE 1

To 40 ml of carbon tetrachloride 32 ml of concentrated sulfuric acid are added with stirring. The solution is cooled to 0° C. and 17.3 g. (0.1 moles) of 2,2,4-trimethyl-1,2-dihydroquinoline are added, whereupon it is kept at an inner temperature of 40° C. The two phases are separated. The lowr phase is extracted with 40 ml of carbon tetrachloride and poured onto ice. Thereafter two 100 ml portions of a 5 N sodium hydroxide solution and 150 ml of a 10 N sodium hydroxide solution are added portionwise followed by the addition of water up to 650 ml. The alkaline solution is extracted with acetone. The acetone phase is evaporated in vacuo and the dark brown solution obtained is poured into ethyl acetate. The suspension obtained is stirred for 1 hour, filtered, washed with a mixture of ethyl acetate and methanol and dried under exclusion of direct elumination. 25.1 g. of (2,2-dimethyl-1,2-dihydroxiquinoline-4-yl)-methylsulfonic acid sodium salt are obtained, melting at 66° to 68° C.

| NMR spectrum: | chemical shift | 6.66–7.5 | 5.9 | 4.1 | 1.33 |
|---|---|---|---|---|---|
| | intensity | 4 | 1 | 2 | 6 |
| | multiplicity | multiplett | | | singulett |

Analysis:
Calculated: C=43.76 H=6.07 N=4.25 Na=6.99 O=29.17 S=9.72
Found: C=42.97 H=5.91 N=4.23 Na=7.00 O=-S=9.53.
Water content (DSC): Calculated: 16.4% Found: 16%

EXAMPLE 2

Into 40 ml of carbon tetrachloride 23.3 g (0.2 moles) of chlorosulfonic acid are added. To the solution 17.3 g (0.1 moles) of 2,2,4-trimethyl-1,2-dihydroquinoline are added at 0° C. It is then kept at 40° C. for 4 hours and then the procedure described in Example 1 is followed. 28.8 g (87.5%) of (2,2-dimethyl-1,2-dihydroquinoline-4-yl)-methylsulfonic acid sodium salt are obtained. The product has the same characteristics as the product of Example 1.

EXAMPLE 3

Following the procedure described in Example 2 but neutralizing the acidic solution obtained after pouring the reaction mixture to ice, with a 5 N sodium hydroxide solution, filling up the neutral mixture to 650 ml with a 35% aqueous calcium acetate solution and finally admixing the suspension obtained with 500 ml of acetone two phases are obtained. After separating the phases the acetone phase is manufactured as described in Example 1 to yield 29.9 g of (2,2-dimethyl-1,2-dihydroquinoline-4-yl)-methylsulfonic acid calcium salt, melting at 72° to 75° C. Yield: 86.6%.

Calcium content: Calculated: 11.3% Found: 11.1%
Water content: Calculated: 15.6% Found: 15.3 (DSC)

EXAMPLE 4

6.5 g. of (2,2-dimethyl-1,2-dihydroquinoline-4-yl)-methylsulfonic acid sodium salt trihydrate in 20 ml. of water are passed through a chromatographic column filled with 120 g of DOWEX 50 WX 10 cation exchanging resin. The column is washed with distilled water and the eluted solution is evaporated. The precipitated substance is filtered, washed with ethyl acetate and dried at room temperature. 4.5 g. (88%) of (2,2-dimethyl-1,2-dihydroquinoline-4-yl)-methylsulfonic acid are obtained, melting at 256° to 260° C.

EXAMPLE 5

Into a solution of 13.2 g. of (2,2-dimethyl-1,2-dihydroquinoline-4-yl)-methylsulfonic acid sodium salt in 10 ml of methanol 2.7 g of zinc chloride are added. The solution is stirred at room temperature of 2 hours, whereupon it is diluted with 40 ml of water. The solution is then evaporated in vacuo on water bath. 9.9 g (87%) of (2,2-dimethyl-1,2-dihydroquinoline-4-yl)-methylsulfonic acid zinc salt are obtained, melting at 98° to 100° C.

EXAMPLE 6

In a counterflow, three-stage quick mixer the following broiler premix is prepared:

| | |
|---|---|
| vitamin A | 1 100 000 NE |
| vitamin D-3 | 220 000 NE |
| vitamin E | 1 500 NE |
| vitamin K | 250 mg |
| vitamin B-1 | 200 mg |
| vitamin B-2 | 600 mg |
| vitamin B-6 | 200 mg |
| vitamin B-12 | 2 mg |
| vitamin C | 1 500 mg |
| Ca—d-pantothenate | 1 300 mg |
| folic acid | 30 mg |
| nicotinic acid | 3 500 mg |
| biotin | 2 mg |
| antioxidant according to Example 1 | 14 000 mg |
| colin chloride | 60 000 mg |
| clopidol (3,5-dichloro-2,6-dimethyl-4-pyridinol) | 12 500 mg |
| Zn SO$_4$ × H$_2$O | in a quantity corresponding to 5200 mg of Zn$^{2+}$ |
| Ca(IO$_3$)$_2$ × H$_2$O | in a quantity corresponding to 100 mg of iodine |
| CoSO$_4$ × 7H$_2$O | in a quantity corresponding to 15 mg of Ca$^{2+}$ |
| MnO (amorphous) | in a quantity corresponding to 6600 mg of Mn$^{2+}$ |
| CuSO$_4$ × 5H$_2$O | in a quantity corresponding to 500 g of Cu$^{2+}$ |
| FeSO$_4$ × 7H$_2$O | in a quantity corresponding to 3000 mg of Fe$^{2+}$ |
| Na$_2$SeO$_3$ | in a quantity corresponding to 8 mg of Se |
| carrier (wheat flour) | ad 1000 g. |

The premix is blended with 100 kg of a fodder mixture, optionally together with phosphorus- and calcium-containing fodder supplements, to form a homogenous mixture.

EXAMPLE 7

In a three-stage, counterflow quick mixer the following premix is prepared for feeding egg-laying poultry.

| | |
|---|---|
| vitamin A | 1 000 000 NE |
| vitamin D-3 | 200 000 NE |
| vitamin E | 1 600 NE |
| vitamin K | 200 mg |
| vitamin B-1 | 200 mg |
| vitamin B-2 | 500 mg |
| vitamin B-6 | 200 mg |
| vitamin B-12 | 2 mg |
| vitamin C | 1 000 mg |
| Ca—d-pantothenate | 1 300 mg |
| folic acid | 30 mg |
| nicotinic acid | 3 000 mg |
| a 2:1 mixture of the compound of Example 1 and Etoxiquin | 12 000 mg |
| colin chloride | 50 000 mg |
| DL-methionin | 40 000 mg |
| ZnSO$_4$ × H$_2$O | in a quantity corresponding to 5200 mg of Zn$^{2+}$ |
| Ca(IO$_3$)$_2$ | in a quantity corresponding to 100 mg of iodine |
| CoSO$_4$ × 7H$_2$O | in a quantity corresponding to 15 mg of Co$^{2+}$ |
| MnO (amorphous) | in a quantity corresponding to 6600 mg of Mn$^{2+}$ |
| CuSO$_4$ × 5H$_2$O | in a quantity corresponding to 500 mg of Cu$^{2+}$ |
| FeSO$_4$ × 7H$_2$O | in a quantity corresponding to 3000 mg of Fe$^{2+}$ |
| Na$_2$SeO$_3$ | in a quantity corresponding to 8 mg of Se |
| carrier (wheat flour) | ad 1000 g |

The premix is blended with 100 kg of fodder mixture, optionally together with phosphorus- and calcium-containing fodder supplements, to form a homogenous mixture.

EXAMPLE 8

The following premix is prepared for feeding hogs:

| | |
|---|---|
| vitamin A | 1 000 000 NE |
| vitamin D-3 | 140 000 NE |
| vitamin E | 1 600 NE |
| vitamin K-3 | 160 mg |
| vitamin B-2 | 500 mg |
| vitamin B-6 | 200 mg |
| vitamin B-12 | 2 mg |
| vitamin C | 250 mg |
| Ca—d-pantothenate | 1 200 mg |
| nicotinic acid | 1 500 mg |
| antioxidant of Example 1 | 1 500 mg |
| colin chloride | 40 000 mg |
| zinc bacitracin | 1 500 mg |
| L-lysine-HCl | 40 000 mg |
| ZnSO$_4$ × H$_2$O | in a quantity corresponding to 9000 mg of Zn$^{2+}$ |
| Ca(IO$_3$)$_2$ | in a quantity corresponding to 100 mg of iodine |

-continued

| | |
|---|---|
| CoSO$_4$ × 7H$_2$O | in a quantity corresponding to 3500 mg of Co$^{2+}$ |
| CuSO$_4$ × 5H$_2$O | in a quantity corresponding to 5000 mg of Cu$^{2+}$ |
| FeSO$_4$ × 7H$_2$O | in a quantity corresponding to 12000 mg of Fe$^{2+}$ |
| carrier (wheat flour) | ad 1000 g |

The premix is homogenously blended with 100 kg of fodder mixture.

EXAMPLE 9

In a two-stage "Nautor" epicyclic mixer the following premix is prepared for feeding milk cuttles.

| | |
|---|---|
| vitamin A | 350 000 NE |
| vitamin D-3 | 300 000 NE |
| antioxidant of Example 3 | 1 000 mg |
| MgO | in a quantity corresponding to 150 000 mg of Mg$^{2+}$ |
| ZnSO$_4$ × H$_2$O | in a quantity corresponding to 14 000 mg of Zn$^{2+}$ |
| Ca(IO$_3$)$_2$ | in a quantity corresponding to 500 mg of iodine |
| MnO (amorphous) | in a quantity corresponding to 9 000 mg of Mn$^{2+}$ |
| CoSO$_4$ × 7H$_2$O | in a quantity corresponding to 600 mg of CO$^{2+}$ |
| CuSO$_4$ × 5H$_2$O | in a quantity corresponding to 2500 mg of Cu$^{2+}$ |
| FeSO$_4$ × 7H$_2$O | in a quantity corresponding to 30 000 mg of Fe$^{2+}$ |
| carrier (wheat flour) | ad 1000 g |

The premix is homogenously blended with 100 kg of fodder, optionally together with phosphorus- and calcium-containing fodder supplements.

EXAMPLE 10

On the basis of the broiler premix obtained in Example 6 the following broiler nutriment is prepared:

| | |
|---|---|
| cob meal | 56.3% |
| wheat meal | 10.0% |
| soy meal (47%, extracted) | 22.0% |
| fish meal (70%) | 8.0% |
| dicalcium phosphate | 1.3% |
| fodder lime | 1.0% |
| fodder salt | 0.4% |
| broiler premix | 1.0% |
| | 100.0% |

EXAMPLE 11

On the basis of the premix obtained in Example 7 the following nutriment is prepared:

| | |
|---|---|
| cob meal | 54.5% |
| wheat meal | 10.0% |
| fish meal (70%) | 1.0% |
| soy meal (47%) | 16.5% |
| extracted sunflower | 3.5% |
| lucerne meal | 5.0% |
| dicalcium phosphate | 1.6% |
| fodder briquette | 6.5% |
| fodder salt | 0.4% |
| premix (Example 7) | 1.0% |
| | 100.0% |

EXAMPLE 12

0.5 parts by weight of the antioxidant prepared in Example 1 are admixed with soy lecinite (50%), whereupon 97 parts by weight of fat are added and the ingredients are admixed homogenously. On the basis of the antioxidant-fat mixture obtained, a rat nutriment described in Example 13 is prepared.

EXAMPLE 13

On the basis of the antioxidant-fat mixture obtained in Example 12 the following rat nutriment is prepared:

| | |
|---|---|
| fish meal (70% crude protein) | 13.0% |
| soy meal (extracted, 47% protein) | 34.0% |
| antioxidant-fat mixture of Example 12 | 4.0% |
| cob meal | 26.0% |
| bran | 8.0% |
| beet sugar | 10.0% |
| mineral materials | 3.0% |
| premix | 2.0% |
| | 100.0% |

EXAMPLE 14

25 g of the antioxidant obtained in Example 1 are homogenously admixed with 975 g of limestone meal and the premix obtained is incorporated into fodder mixtures in a quantity of 1%.

EXAMPLE 15

16 g of the antioxidant obtained in Example 1 are admixed with 9 g of Etoxiquin adsorbed on 4 g of silica. The premix obtained is incorporated into fodder mixtures in a quantity of 0.5%.

TABLE 1

Protection of sunflower oil from becoming rancid peroxid number

| Days | without anti-oxidant | 250 ppm of XAX | 250 ppm of Etoxi-quin | 250 ppm of BHT | 250 ppm of the anti-oxidant of Example 1 | 250 ppm of a 2:1 mixture of the anti-oxidant of Example 1 | 1000 ppm of the anti-oxidant of Example 1 |
|---|---|---|---|---|---|---|---|
| 1 | 2 | 1 | 1 | 1 | 1 | 1 | 0 |
| 2 | 12 | 9 | 8 | 8 | 7 | 6 | 2 |
| 7 | 24 | 20 | 17 | 18 | 15 | 13 | 5 |
| 12 | 55 | 45 | 39 | 37 | 35 | 33 | 11 |
| 15 | 90 | 68 | 58 | 55 | 54 | 55 | 16 |
| 18 | 139 | 96 | 81 | 76 | 72 | 76 | 19 |

XAX 2 methylene-bis-(2,2,4-trimethyl-1,2-dihydroquinoline)
Etoxiquin = 6-ethoxy-2,2,4-trimethyl-1,2-dihydroquinoline
BHT = 2,6-di-tert.-butyl-4-methylphenol

TABLE 2

Change in the carotin concentration of lucerna meal

Cartotin mg/kg

| Days | without anti-oxidant | 250 ppm of BHT | 250 ppm of the antioxidant of Example 1 |
|---|---|---|---|
| 1 | 135 | 137 | 138 |
| 7 | 114 | 124 | 131 |
| 28 | 80 | 98 | 112 |
| 49 | 57 | 71 | 92 |
| 70 | 34 | 46 | 84 |

We claim:
1. (2,2-Dimethyl-1,2-dihydroquinoline-4-yl)-methylsulfonic acid or a salt thereof.
2. An alkali metal or alkaline earth metal salt of (2,2-dimethyl-1,2-dihydroquinoline-4-yl)-methylsulfonic acid.
3. A sodium, ammonium, calcium or zinc salt of (2,2-dimethyl-1,2-dihydroquinoline-4-yl)-methylsulfonic acid.

* * * * *